United States Patent
Banner et al.

(10) Patent No.: US 6,450,164 B1
(45) Date of Patent: Sep. 17, 2002

(54) ENDOTRACHEAL TUBE PRESSURE MONITORING SYSTEM AND METHOD OF CONTROLLING SAME

(76) Inventors: Michael J. Banner, 14727 NW. 60 Ave., Alachua, FL (US) 32615; Paul B. Blanch, 15214 NW. 94 Ave., Alachua, FL (US) 32615; Neil R. Euliano, 3914 SW. 95 Dr., Gainesville, FL (US) 32608

( * ) Notice: Subject to any disclaimer, the term of this patent is extended or adjusted under 35 U.S.C. 154(b) by 100 days.

(21) Appl. No.: 09/641,986

(22) Filed: Aug. 17, 2000

(51) Int. Cl.⁷ .............................................. F16K 31/02
(52) U.S. Cl. ............................ 128/204.21; 128/207.15
(58) Field of Search ....................... 128/200.24, 200.18, 128/204.22, 204.23, 207.14, 207.15, 204.21

(56) References Cited

U.S. PATENT DOCUMENTS

| | | |
|---|---|---|
| 4,214,593 A | 7/1980 | Imbruce et al. |
| 5,218,970 A * | 6/1993 | Turnbull et al. ....... 128/207.15 |
| 5,546,935 A | 8/1996 | Champeau |
| 5,752,921 A | 5/1998 | Orr |
| 5,906,204 A | 5/1999 | Beran et al. |
| 6,315,739 B1 * | 11/2001 | Merilainen et al. ......... 600/587 |

* cited by examiner

Primary Examiner—Glenn K. Dawson
(74) Attorney, Agent, or Firm—Needle & Rosenberg, P.C.

(57) ABSTRACT

An endotracheal tube pressure monitoring system for an endotracheal tube having at least one pressure line in fluid communication with a major lumen of the endotracheal tube, a purging subsystem in fluid communication with at least one of the pressure lines, and a pressure monitoring subsystem in operative communication with each respective pressure line to monitor the pressure of fluid within each respective pressure line. Each pressure line that is in fluid communication with the purging subsystem being selectively purged by the purging subsystem when pressure monitoring subsystem determines the respective pressure line has become obstructed. Purging the pressure line maintains the patency of the pressure line so that accurate pressure measurements within the endotracheal tube can be obtained for calculation of parameters in lung mechanics. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

30 Claims, 7 Drawing Sheets

ENDOTRACHEAL TUBE PRESSURE MONITORING SYSTEM AND METHOD OF CONTROLLING SAME

BACKGROUND OF THE INVENTION

1. Field of the Invention

The present invention relates to a system and methods used to determine pressure measurements within an endotracheal tube for use in calculation of parameters in lung mechanics and for use in determining the patency of the endotracheal tube. More specifically, the present invention is related to a system and methods for maintaining the patency of at least one pressure line in fluid communication with a major lumen of an endotracheal tube to ensure the viability of pressure measurements from the pressure line for subsequent use in calculation of parameters in lung mechanics and for use in determining the patency of the endotracheal tube, particularly for patients who are connected to a ventilator.

2. Background Art

Endotracheal pressure measurements are needed to calculate lung mechanics, for example, the calculation of work of breathing, lung compliance, and airway breathing. Such pressure measurements may also be used to assist in controlling the breathing support supplied by a ventilator, for example, the use of pressure support ventilation, demand flow ventilation and tracheal pressure control ventilation. These pressure measurements are particularly needed in patient's undergoing surgery and/or in a condition requiring connection to a ventilator.

Ventilators are commonly employed to assist the patient in breathing and typically include two main lines which are independently connected from the ventilator to separate branched arms from a Y-tube junction. A connector is inserted into the open stem of the Y-tube for further connection with an endotracheal tube or tracheostomy tube extending from the trachea of the patient. The main lines, the Y-tube and the connector form a breathing circuit to provide the necessary breathing support required by the condition of the patient. Airway pressure, which is the air pressure within the endotracheal tube proximate the proximal end of the endotracheal tube and may be used in such calculation of lung mechanics, is typically measured at the connection between the endotracheal tube and the breathing circuit. More particularly, it is typically measured between the endotracheal tube and the Y-tube of the breathing circuit.

At an appropriate pressure support ventilation level, the total work of breathing of the patient is shared between the ventilator and the patient. For the ventilator to perform a portion of the work of breathing, an appropriate level of pressure support ventilation must be preselected. To set the ventilator properly and relieve the patient's work of breathing, tracheal pressure must be accurately measured to calculate the imposed resistive work of breathing. The tracheal pressure is the air pressure within the endotracheal tube proximate the distal end of the endotracheal tube, i.e., proximate the trachea of the patient. During demand-flow spontaneous ventilation and tracheal pressure control ventilation, the patient must perform some desired portion of the work of breathing and generally must create a negative pressure to initiate a breath. Using tracheal pressure or a combination of tracheal pressure and the airway pressure measured at the connection between the endotracheal tube and the breathing circuit as the triggering pressure decreases the response time in initiating the breath and the patient's work of breathing.

Tracheal pressure can be measured by placing a catheter down the endotracheal tube or by using an endotracheal tube having a secondary lumen in the endotracheal tube wall, which is open at the distal end of the endotracheal tube. The catheter and the secondary lumen are subject to kinking and mucosal blockage. Tracheal pressure can be significantly lower than airway pressure and the pressure difference can change if the pressure lines that are in fluid communication with the distal and/or proximal ends of the endotracheal tube become obstructed or partially obstructed with water, or mucous, or kinked, any of which can shut off or limit the flow of fluid through the respective pressure line. Obstructions within the pressure lines may result in erroneous tracheal and/or airway pressure readings. Without the correct pressure measurements of tracheal pressure and/or airway pressure, the derived data based on the incorrect pressure measurements are predisposed to be in error, which may result in insufficient ventilation of the patient.

Additionally, if the endotracheal tube itself becomes obstructed with water or mucous or kinked, the flow of air delivered to the patient can be limited or shut off, which would insufficiently ventilate the lungs of the patient. Patency of the endotracheal tube may be determined by comparing the pressure of the fluid at the distal end of the endotracheal tube, i.e., the tracheal pressure, to the pressure of the fluid at the proximal end of the endotracheal tube, i.e., the airway pressure. However, the measurement of these pressures may be adversely affected by water or mucosal blockages within the respective pressure lines.

SUMMARY

The present invention relates to a pressure monitoring system for an endotracheal tube. The endotracheal tube has an open distal end, an opposing open proximal end, and a major lumen extending within the tube from the proximal end to the distal end. The distal end of the endotracheal tube is in fluid communication with a trachea of a patient.

The pressure monitoring system has at least one pressure line, a purging subsystem, and a pressure monitoring subsystem. Each pressure line is in fluid communication with the major lumen of the endotracheal tube. The purging subsystem is in fluid communication with at least one of the pressure lines. The pressure monitoring subsystem is in operative communication with each pressure line and has means to monitor the pressure of fluid within each respective pressure line.

For each pressure line in that is in fluid communication with the purging subsystem, the pressure monitoring subsystem may generate a response signal in response to a determined pressure within the pressure line which indicates that the pressure line is obstructed. In response to the response signal generated by the pressure monitoring subsystem, the purging subsystem supplies a pressurized fluid to the pressure line with which the purging subsystem is in fluid communication. This pressurized fluid clears the obstruction from the pressure line so that accurate pressure readings may be obtained from the pressure line. After a predetermined time period subsequent to the generation of the response signal, the pressure monitoring subsystem terminates the supply of the pressurized fluid to the pressure line.

In one embodiment, the pressure lines may include a first pressure line that is in fluid communication with the distal end of the endotracheal tube so that a tracheal pressure may be measured. Because of the high probability of blockage due to its proximity to the trachea and lungs of the patient, this first pressure line may also be in fluid communication with the purging subsystem so that the patency of the first pressure line may be maintained. Alternatively, in another embodiment, the pressure lines may include a second pressure line that is in fluid communication with the proximal end of the endotracheal tube. This second pressure line enables the measurement of airway pressure. The second pressure line may also be in fluid communication with the purging subsystem.

DETAILED DESCRIPTION OF THE DRAWINGS

Figure 5:
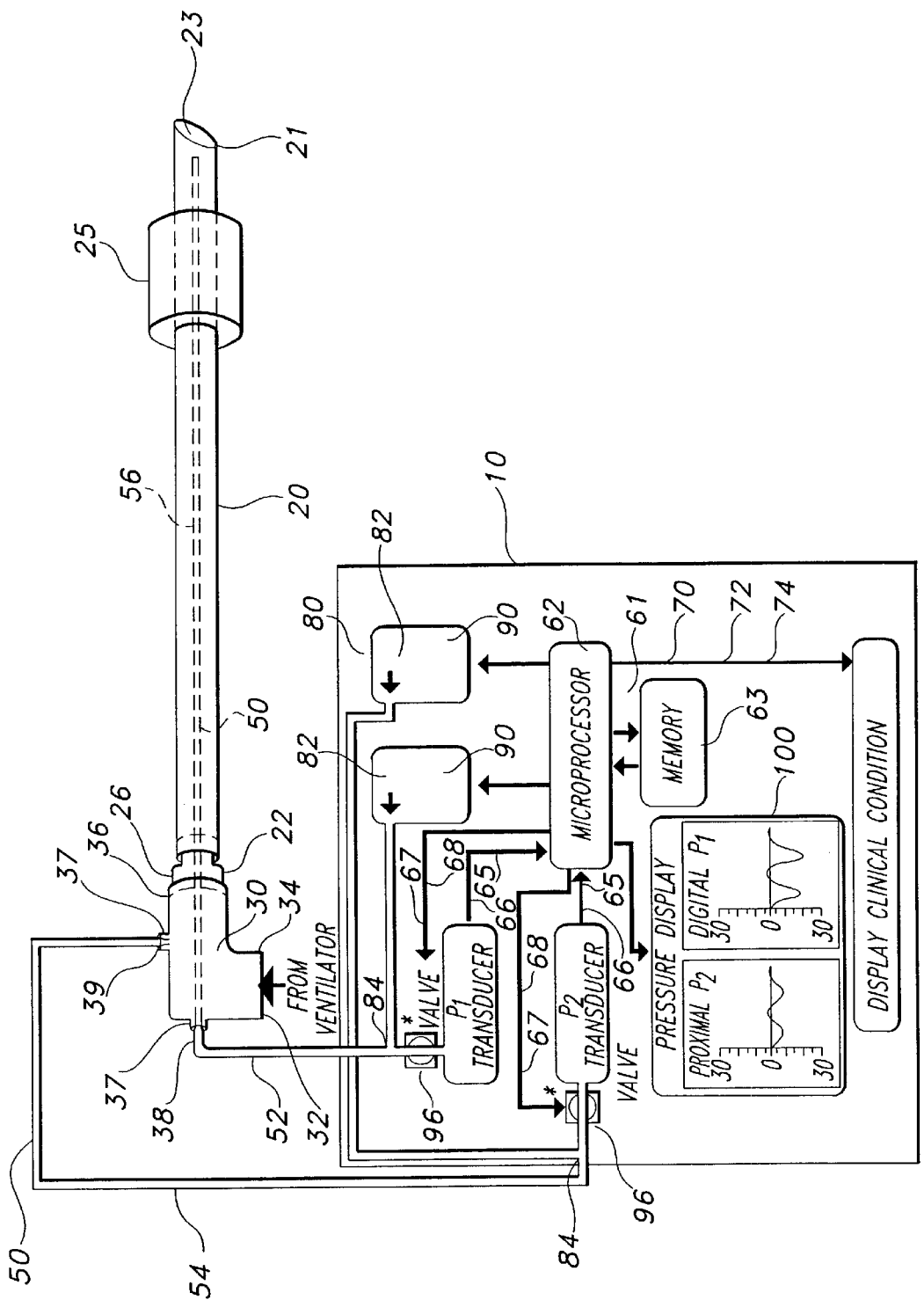

FIG. 5 is a schematic view of a fourth embodiment of the endotracheal tube pressure monitoring system showing the first pressure line in fluid communication with the distal end of the endotracheal tube and in fluid communication with the purging subsystem, and the second pressure line in fluid communication with a proximal end of the endotracheal tube and in fluid communication with the purging subsystem, and showing a connector attached to the proximal end of the tracheal tube for the operative connection of the second pressure line and for the insertion of a secondary lumen forming a portion of the first pressure line.

Figure 6:
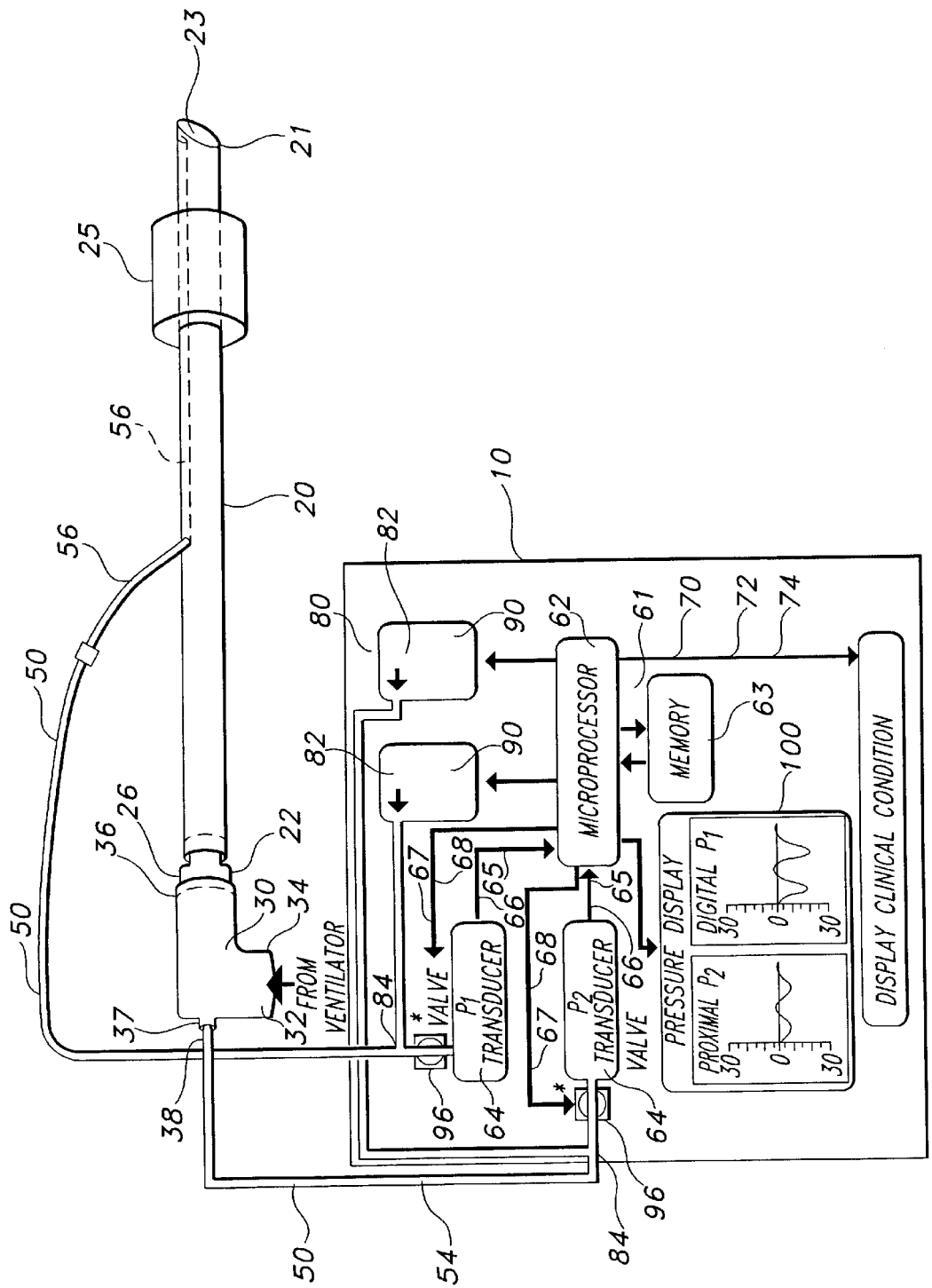

FIG. 6 is a schematic view of the fourth embodiment of the endotracheal tube pressure monitoring system showing the second pressure line in operable connection to a port in the connector and showing a secondary lumen in the endotracheal tube wall that forms a portion of the first pressure line.

Figure 7:
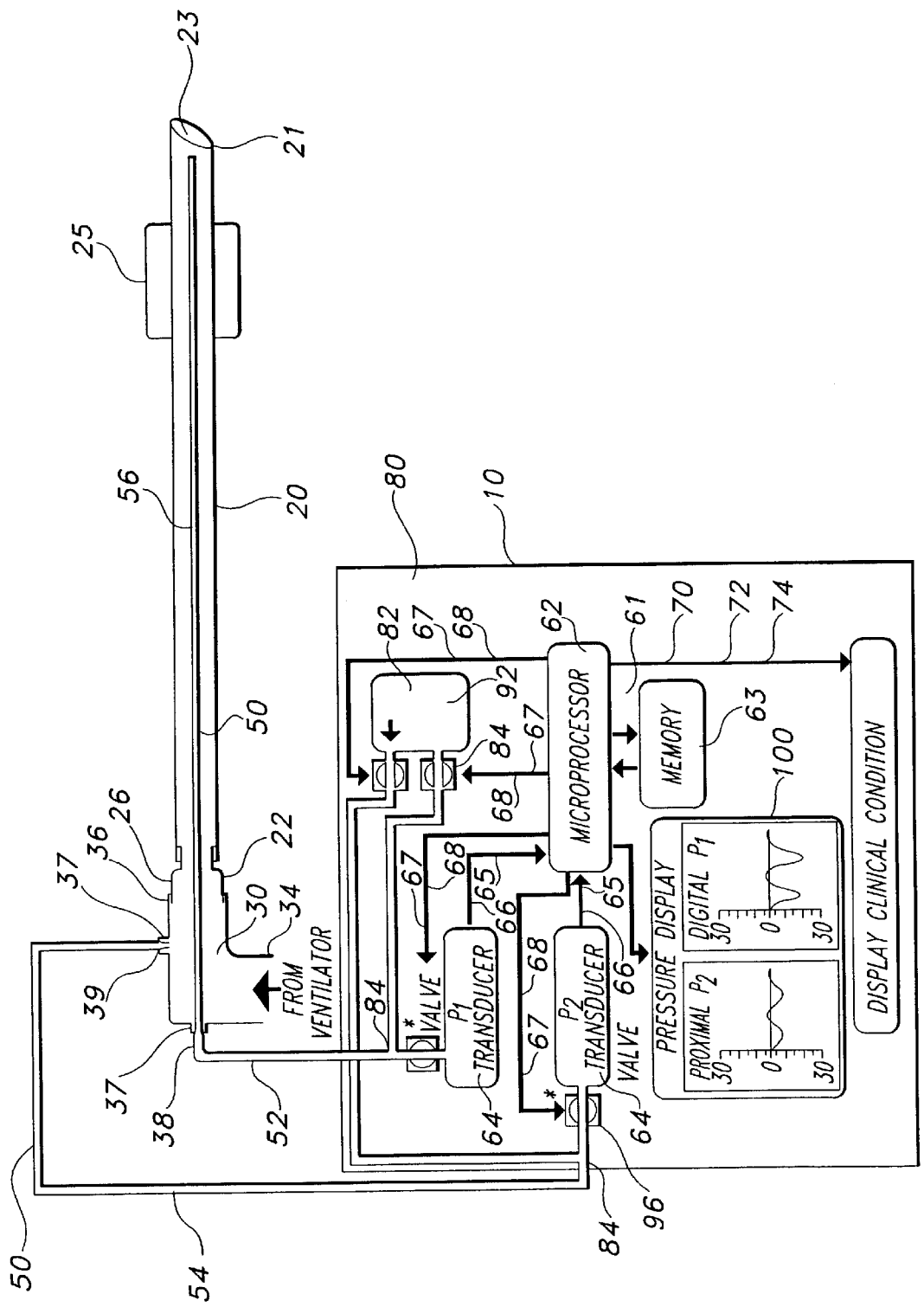

FIG. 7 is a schematic view of a fifth embodiment of the endotracheal tube pressure monitoring system showing the first and second pressure lines in fluid communication with a vessel of compressed fluid.

DETAILED DESCRIPTION OF THE INVENTION

The present invention is more particularly described in the following examples that are intended as illustrative only since numerous modifications and variations therein will be apparent to those skilled in the art. Thus, the embodiments of this invention described and illustrated herein are not intended to be exhaustive or to limit the invention to the precise form disclosed. They are chosen to describe or to best explain the principles of the invention and its application and practical use to thereby enable others skilled in the art to best utilize the invention. As used in the specification and in the claims, "a," "an," and "the" can mean one or more, depending upon the context in which it is used. Reference will be made to the present embodiments of the invention, whenever possible, the same reference numbers are used throughout to refer to the same or like parts.

Figure 1:
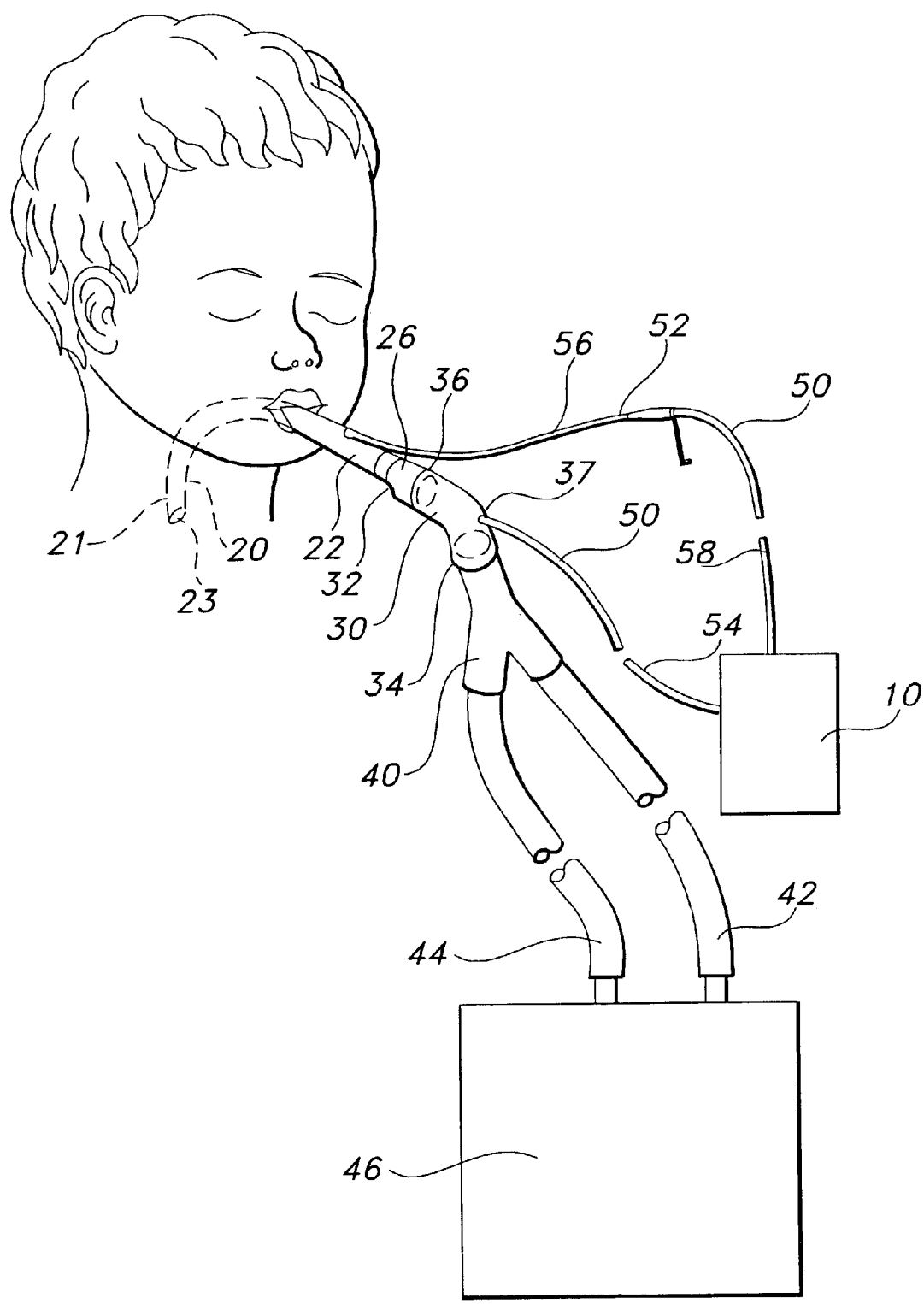
FIG. 1 is a view of the endotracheal tube pressure monitoring system showing an endotracheal tube connected to a breathing circuit of a ventilator.

Referring to FIG. 1, an endotracheal tube pressure monitoring system 10 is disclosed with an appropriately-sized endotracheal tube 20 (or tracheostomy tube) being chosen in sizes appropriate to the anatomical and physiological requirements of the patient. Any standard endotracheal tubes 20 may be used with the present invention. As one skilled in the art will appreciate, the term "endotracheal tube" is used generically to refer to any tubular conduit that may be inserted into a trachea of a patient for fluid communication with the trachea; for example, any standard endotracheal tube 20 or tracheostomy tube may be utilized. The endotracheal tube 20 has an open distal end 21, an opposing open proximal end 22, and a major lumen 23 extending within the tube 20 from the proximal end 22 to the distal end 21. The endotracheal tube 20 may have a balloon cuff 25 extending around the circumference of the exterior surface of the endotracheal tube wall between the proximal and distal ends 22, 21. The balloon cuff 25 may be inflated when the endotracheal tube 20 is placed into the trachea so that the trachea is sealed except for the fluid access provided by the endotracheal tube 20. The endotracheal tube 20 generally has an attachment member 26 that forms the proximal end 22 of the endotracheal tube 20. This attachment member 26 typically has a cylindrical attachment collar that has an outside diameter adapted to provide a frictional fit with a connector 30 of a ventilator breathing circuit.

Alternatively, for example, and as shown in FIGS. 1 and 6, the endotracheal tube 20 may also have a secondary lumen 56 in the endotracheal tube wall that extends at least partially along the length of the endotracheal tube 20. The secondary lumen 56 within the tube wall has a diameter that is smaller than the diameter of the major lumen 23 of the endotracheal tube 20. The secondary lumen 56 of this example has an opening communicating with the major lumen 23 of the endotracheal tube 20 near the distal end 21 of the endotracheal tube 20. In this type of endotracheal tube 20, the secondary lumen 56 typically passes through the endotracheal tube wall to the exterior of the endotracheal tube 20 at some point intermediate the proximal and distal ends 22, 21 of the endotracheal tube 20.

As can be seen in FIG. 1, the ventilator breathing circuit also includes a Y-tube connector 40 that is frictionally fit to the connector 30 and is respectively connected to an inhalation tube 42 and an exhalation tube 44 that are, in turn, connected to a ventilator 46. Referring to FIGS. 1–7, the connector 30 is a known type and typically has a tubular conduit 32 extending from a first end 34 to an opposing second end 36. The connector 30 has an inside diameter sized to provide a frictional fit between the first end 34 and the Y-tube connector 40 of the ventilator breathing circuit and to provide a frictional fit between the second end 36 and the attachment member 26 (i.e., with the proximal end 22 of the endotracheal tube 20). The connector 30 may have one or more ports 37 that are in communication with the tubular conduit 32. As one skilled in the art will appreciate, when the connector 30 is attached to the proximal end 22 of the endotracheal tube 20, the ports 37 are in fluid communication with the major lumen 23 of the endotracheal tube 20. Typically, the connector 30 has a "L"-shape in cross-section to form a right-angled connector 30.

Referring generally to FIGS. 1–7, the endotracheal tube pressure monitoring system 10 of the present invention generally comprises at least one pressure line 50 in fluid communication with the major lumen 23 of the endotracheal tube 20, a purging subsystem 80 in fluid communication with at least one pressure line 50, and a pressure monitoring subsystem 60 in operative communication with each of the pressure lines 50 of the system 10.

Each pressure line 50 is formed from one or more tubular conduits. At least a portion of each pressure line 50 is in fluid communication with the major lumen 23 of the endotracheal tube 20. For example, a portion of the pressure line 50 may be in fluid communication with the distal end 21 of the endotracheal tube 20 so that the pressure monitoring subsystem 60 is in operative communication with the distal end 21 of the endotracheal tube 20. In another example, a portion of the pressure line 50 may be in fluid communication with the proximal end 22 of the endotracheal tube 20 so that the pressure monitoring subsystem 60 is in operative communication with the proximal end 22 of the endotracheal tube 20.

The pressure line 50, for example, may be formed from a connector tube 58, a secondary lumen 56, or a connected combination of the connector tube 58 and a secondary lumen 56. The secondary lumen 56 has a diameter smaller than the major lumen 23 of the endotracheal tube 20. In one example, if the pressure of the fluid proximate the distal end 21 of the endotracheal tube 20 is desired to be measured, i.e., the tracheal pressure, then at least a portion of the pressure line 50 may be formed from the secondary lumen 56, such as, for example, a catheter, extending within the endotracheal tube 20 from the distal end 21 of the endotracheal tube 20 (more particularly, the secondary lumen 56, such as the catheter, may extend through one of the ports 37 of the connector 30 to the distal end 21 of the endotracheal tube 20). To communicate the fluid to the pressure monitoring subsystem 60, the secondary lumen 56 may be connected to the pressure monitoring subsystem 60 or may be connected to the connector tube 58 which is, in turn, connected to the pressure monitoring subsystem 60.

In an alternative example, if the endotracheal tube 20 has an integral secondary lumen 56 embedded within the endotracheal tube 20 side wall, as described above, then at least a portion of the pressure line 50 may comprise the integral secondary lumen 56. To communicate the fluid within the formed pressure line 50 to the pressure monitoring subsystem 60, the integral secondary lumen 56 of this example may be connected to the pressure monitoring subsystem 60 or may be connected to the connector tube 58 which is, in turn, connected to the pressure monitoring subsystem 60. In yet another example, to measure the airway pressure proximate the proximal end 22 of the endotracheal tube 20, one pressure line 50 may be connected to one of the ports 37 of the connector 30 and to the pressure monitoring subsystem 60 to communicate the fluid within the formed pressure line 50 to the pressure monitoring subsystem 60.

From the examples noted above, as one skilled in the art will appreciate, the connector 30 may be used to facilitate the measurement of airway pressure proximate the proximal end 22 of the endotracheal tube 20 by allowing the connection of the pressure line 50 to a first port 38 of the connector 30, which is adjacent the proximal end 22 of the endotracheal tube 20 and to the pressure monitoring subsystem 60. The connector 30 may also facilitate the measurement of the tracheal pressure of the fluid proximate the distal end 21 of the endotracheal tube 20 by inserting the secondary lumen 56, such as the catheter, through a second port 39 of the connector 30 so that the distal end of the secondary lumen 56 is proximate the distal end 21 of the endotracheal tube 20 and connecting the secondary lumen 56 to the pressure monitoring subsystem 60.

The pressure monitoring subsystem 60 of the endotracheal tube pressure monitoring system 10 is in fluid communication with each pressure line 50 of the system and has a means for monitoring the pressure within each respective pressure line 50. The pressure monitoring means includes a computing apparatus 61 and at least one pressure sensor 64. Each pressure line 50 has a pressure sensor 64 operatively attached (i.e., disposed in the flow path of the fluid within the pressure line 50) for sensing the pressure of the fluid within the pressure line 50. The pressure sensor 64 generates a pressure signal 65 representative of the pressure of the fluid proximate the pressure sensor 64. The pressure signal 65 may be transmitted through an A/D converter (not shown) to the computing apparatus 61 on pressure signal line 66. This pressure signal 65 may be transmitted through a digital or analog anti-aliasing filter (not shown) to remove noise above the Nyquist frequency before processing.

The pressure sensor 64 may be any known pressure sensor 64, for example, a pressure transducer, a piezoresistive pressure sensor, a solid state pressure sensor, or the like. The pressure sensor 64 may, for example, use commercially available pressure sensors from Microswitch, Honeywell or Sensym. Any pressure sensor 64 capable of sensing the pressure of the fluid proximate the pressure sensor 64 and providing a signal representative of that pressure sensed could be substituted as the pressure sensor 64. For example, an aneroid pressure manometer could be a suitable substitute.

The computing apparatus 61 of the pressure monitoring subsystem 60 preferably comprises a processor 62, for example, a microprocessor, a hybrid hardware/software system, controller, computer, neural network circuit, digital signal processor, digital logic circuits, or an application specific integrated circuit (ASIC), and a memory 63. The computing apparatus 61 is electronically coupled to each pressure sensor 64 via the pressure signal line 66. The processor 62 of the computing apparatus 61 may be analog or digital and should contain circuits to be programed for performing mathematical functions such as, for example, waveform averaging, amplification, linearization, signal rejection, differentiation, integration, addition, subtraction, division, multiplication, and the like where desired. If an analog processor is used, the A/D converter is not required, because the analog processor requires the pressure signal to be in the non-converted analog format.

The parameters and data derived from the pressure signal(s) 65 produced by the pressure sensor(s) 64 are stored in the memory 63 of the computing apparatus 61 at user-defined rates, which may be continuous, for as-needed retrieval and analysis. The parameters and data may include one or more of: the pressure of the fluid within the endotracheal tube 20 proximate the distal end 21 of the endotracheal tube 20 (the tracheal pressure, P1); the pressure of the fluid within the endotracheal tube 20 proximate the proximal end 22 of the endotracheal tube 20 (the airway pressure, P2); the trended P1 data; the trended P2 data; and patency status of the endotracheal tube 20 and/or the pressure line(s) 50. The pressure sensor(s) 64 may continually monitor/sense the pressure of the fluid proximate the respective sensor(s) 64. The memory 63 may be, for example, a floppy disk drive, a CD drive, internal RAM, or a hard drive of the associated processor. The parameters and data may be stored to provide a permanent log of parameters and data stored that relate to the patient's course on the ventilator, and allow for on-line and retrospective analysis of the patency of the endotracheal tube 20. As one skilled in the art will appreciate, any generated signal may be stored in the memory at user-defined rates.

The purging subsystem 80 of the system 10 comprises at least one source of pressurized fluid 82 that is in fluid communication with at least one pressure line 50 at a juncture 84 in the respective pressure line 50 so that a pressurized fluid may be supplied to the pressure line 50 with which it is connected. Preferably, the pressurized fluid is pressurized to at least exceed the ambient pressure of the fluid within the respective pressure line 50 so that the pressurized fluid can pass through the pressure line 50 in a direction opposite the normal flow. More preferably, the pressurized fluid is pressurized to at least exceed the pressure drop across the respective pressure line 50. Most preferably, the pressurized fluid is pressurized to at least exceed twice the pressure drop across the respective pressure line 50. The "opposite" flow provided by the applied pressurized fluid allows the pressurized fluid to dislodge and remove any obstructions that may be interfering with, blocking, or obstructing the normal flow of fluid through the pressure line 50. The source of pressurized fluid 82 is responsive to the pressure monitoring subsystem 60 and may be, for example, a fluid pump 90 or a vessel of compressed fluid 92.

The vessel of compressed fluid 92 may, for example be a line of compressed fluid that is typically contained in hospital room walls, such as, pressurized oxygen or air lines, or may be a self-contained vessel of pressurized fluid. The vessel of compressed fluid 92 has at least one fluid actuator 94. The fluid actuator 94 is responsive to the pressure monitoring subsystem 60 to communicate pressurized fluid on demand to the pressure line 50 with which the vessel 92 is connected. One fluid actuator 94 is operatively connected to the respective pressure line 50 intermediate the juncture 84 and the vessel of compressed fluid 92. Each fluid actuator 94 preferably defines a passage (not shown) through which the pressurized fluid contained in the vessel 92 traverses to reach the pressure line 50 and a fluid actuator control means for adjusting the passage to change the flow of fluid therethrough.

The fluid actuator control means adjusts the passage within the fluid actuator 94 in response to signals from the pressure monitoring subsystem 60. The fluid actuator 94 is preferably a binary valve, which is in either a fully open or fully closed position. In the closed position, which is the normal operating condition, the pressurized fluid within the vessel 92 cannot communicate to its connected pressure line 50. In the open position, which occurs during purging operations, the pressurized air from the vessel 92 is introduced into the pressure line 50 to remove obstructions from the pressure line 50. Such a fluid actuator 94 may also be utilized in combination with the fluid pump 90 to communicate pressurized fluid on demand to the pressure line 50 with which the fluid pump 90 is connected.

If the pressure sensors 64 are prone to damage by the pressure of the pressurized fluid supplied by the source of pressurized fluid 82, the purging subsystem 80 may include at least one purging actuator 96. The purging actuator 96 preferably operates in a similar manner to the fluid actuator 94 described above. That is, one purging actuator 96 is operatively connected to the pressure line 50 intermediate the pressure sensor 64 and the juncture 84 in the pressure line 50. Each purging actuator 96 preferably defines a passage (not shown) through which the fluid within the pressure line 50 traverses to reach the pressure sensor 64 and a purging actuator control means for adjusting the passage to change the rate of flow of the fluid therethrough. The purging actuator control means adjusts the passage within the purging actuator 96 in response to signals from the pressure monitoring subsystem 60. Like the fluid actuator 94, the purging actuator 96 is preferably a binary valve, which is in either a fully open or fully closed position. In the open position, which is the normal operating condition, the fluid within the respective pressure line 50 communicates with the pressure sensor 64 that is operably connected to that respective pressure line 50. In the closed position, which is used during purging operations, fluid within the respective pressure line 50 is prevented from communicating with the pressure sensor 64. Thus, when the purging subsystem 80 is activated, pressurized fluid is introduced into the pressure line 50 and the closed purging actuator 96 protects the connected pressure sensor 64 by preventing the introduced pressurized fluid from making contact with the pressure sensor 64.

The endotracheal tube 20 pressure monitoring system 10 may further have a visual display 100 or CRT, electronically coupled to the computing apparatus 61 for outputting and displaying electronic signals generated from the computing apparatus 61. The visual display 100 may vary the pattern of the display in accordance with the contents of the electronic output signals from the computing apparatus 61. Preferably, the visual display 100 is a monitor but any means for displaying electronic output signals known to one skilled in the art may be used.

Still further, the endotracheal tube pressure monitoring system 10 may have an alarm 110 for alerting the operator of either a failure in the endotracheal tube pressure monitoring system 10, such as a power failure, or of a patency failure or degradation of the pressure line(s) 50 or the endotracheal tube 20. The alarm 110 may be any suitable alarm, however, preferably, the alarm 110 has a visual and/or audio alarm for alerting the operating clinician. Of course, it is desired to include a backup power supply, such as a battery.

The pressure monitoring subsystem 60 of the present invention is responsive to the pressure signal(s) to determine, preferably continuously, the pressure within the respective pressure line 50 and to determine, based on the determined pressure, the patency status of the respective pressure line 50. The pressure monitoring subsystem 60 compares the trended pressure within the respective pressure line 50 over a first predetermined period of time and generates a response signal 67 based on that comparison. The preferred first predetermined period of time is the time required for the patient to complete from 2 to 10 breaths; more preferably, the first predetermined period of time is the time required for the patient to complete from 2 to 6 breaths; most preferably, first predetermined period of time is the time required for the patient to complete from 2 to 4 breaths. Typically, an adult will complete a single breath in approximately 3 second, approximately 1 second to inhale and approximately 2 seconds to exhale.

The pressure monitoring subsystem 60 generates the response signal 67 when the determined pressure within the respective pressure line 50 remains substantially constant for the first predetermined period of time. That is, if the determined pressure acutely freezes in place or remains substantially zero for the first predetermined period of time, the respective pressure line 50 is obstructed and the pressure monitoring subsystem 60 generates the response signal 67. Then, in response to the response signal 67, the alarm 110 may generate a signal that is suitable for alerting the operator that the pressure line 50 is obstructed. In a further response to the response signal 67, if the obstructed pressure line 50 is in fluid communication with the purging subsystem 80, the operative components of the purging subsystem 80 (as described above) are activated to purge the obstructed pressure line 50 of the obstruction.

When activated, the purging subsystem 80 supplies pressurized fluid to the obstructed pressure line 50 for a second predetermined period of time. Preferably, the second predetermined period of time is between approximately 0.3 to 6 seconds; more preferably is between approximately 0.3 to 4 seconds; and most preferably is between approximately 0.5 to 2 seconds. Upon the lapse of the second predetermined period of time, the purging subsystem 80 is deactivated and the components of the purging subsystem 80 are returned to their normal operative positions, which terminates supply of the pressurized fluid to the pressure line 50 with which the purging subsystem 80 is in fluid communication and allows fluid from the major lumen 23 of the endotracheal tube 20 to fluidly communicate with the pressure sensor 64. The purging subsystem 80 may automatically be de-activated at the expiration of the second predetermined period of time. However, it is preferred that the pressure monitoring subsystem 60 generate a termination signal 68 after the second predetermined period of time lapses. Then, in response to the termination signal 68 of the pressure monitoring subsystem 60, the purging subsystem 80 terminates supply of the pressurized fluid to the pressure line 50 with which the purging subsystem 80 is in fluid communication. As one skilled in the art will appreciate, the system 10 continuously monitors the pressure within the respective pressure line 50 and will cycle the purging subsystem 80 on and off whenever the requirements for the generation of the response signal 67 are met. For example, if an obstruction is detected in the pressure line 50, the system 10 will continue to cycle the purging subsystem 80 until the obstruction is cleared (initially out of the affected pressure line 50 into the major lumen 23 of the endotracheal tube 20), by activating and de-activating the purging subsystem 80 in response to the pressure monitoring subsystem 60.

When the purging subsystem 80 is activated in response to the response signal 67, the source of pressurized fluid 82 supplies pressurized fluid to the obstructed pressure line 50 with which the purging subsystem 80 is attached. That is, if a fluid pump 90 is the source of pressurized fluid, the fluid pump 90 is activated and the fluid actuator 94, if used, is turned to the open position to provide pressurized fluid from the fluid pump 90 to the obstructed pressure line 50. If a purging actuator 96 is operably attached to the pressure line 50, the purging actuator 96 is turned to the closed position so that no pressurized fluid is communicated to the pressure sensor 64 attached to the obstructed pressure line 50. Similarly, if the vessel of compressed fluid 92 is the source of pressurized fluid 82, the fluid actuator 94 is turned to the open position to provide pressurized fluid from the vessel 92 to the obstructed pressure line 50 and, if a purging actuator 96 is operably attached to the obstructed pressure line 50, the purging actuator 96 is turned to the closed position so that no pressurized fluid can be communicated to the pressure sensor 64 attached to the obstructed pressure line 50. Preferably, the fluid pump 90, the fluid actuator 94, the purging actuator 96 (in whatever combination used) of the purging subsystem 80 are activated and appropriately positioned substantially simultaneously.

In the same fashion, when the purging subsystem 80 is de-activated in response to the termination signal 68 or the lapse of the second predetermined time, the supply of pressurized fluid from the source of pressurized fluid 82 to the pressure line 50 with which the purging subsystem 80 is attached is terminated. That is, if a fluid pump 90 is the source of pressurized fluid 82, the fluid pump 90 is deactivated and the fluid actuator 94, if used, is turned to the closed position to terminate the supply of the pressurized fluid to the pressure line 50. If a purging actuator 96 is operably attached to the pressure line 50, the purging actuator 96 is turned to the open position so that fluid within the pressure line 50 may be placed in fluid communication with the pressure sensor 64 attached to the respective pressure line 50. Similarly, if the vessel of compressed fluid 92 is the source of pressurized fluid 82, the fluid actuator 94 is turned to the closed position to terminate the supply of the pressurized fluid to the pressure line 50 and, if a purging actuator 96 is operably attached to the obstructed pressure line 50, the purging actuator 96 is turned to the open position so that fluid within the pressure line 50 can be communicated to the pressure sensor 64 attached to the pressure line 50. Preferably, the fluid pump 90, the fluid actuator 94, the purging actuator 96 (in whatever combination used) of the purging subsystem 80 are de-activated and appropriately positioned substantially simultaneously.

The pressure monitoring subsystem 60 of the present invention may also be responsive to the pressure signals to determine, preferably continuously, the pressures within the respective pressure lines 50 and to determine, based on the determined pressures, the patency status of endotracheal tube 20. In this embodiment, the pressure lines 50 include a first pressure line 52 and a second pressure line 54. The first pressure line 52 is in fluid communication with the distal end 21 of the endotracheal tube 20 and the measured pressure within the first pressure line 52 is indicative of the tracheal pressure (P1). As described above, at least a portion of the first pressure line 52 may be formed from the secondary lumen 56 or catheter. The second pressure line 54 is in fluid communication with the proximal end 22 of the endotracheal tube 20 and the measured pressure within the second pressure line 54 is indicative of the airway pressure (P2). As described above, the second pressure line 54 may be connected to a port in the connector 30 to provide the necessary fluid access to the proximal end 22. The pressure monitoring subsystem 60 compares the measured pressures and/or the trended pressures within the first and/or second pressure lines 52, 54 over a third predetermined period of time to determine the patency of the endotracheal tube 20. The pressure monitoring subsystem 60 generates an output signal if the patency of the endotracheal tube 20 is determined to be degraded. In response to the output signal, the alarm 110 may be activated to alert an operator of the degraded status of the endotracheal tube 20. Further, the output signal may be output to the visual display 100 for display to the operator of the clinical condition of the endotracheal tube 20.

The preferred third predetermined period of time is the time required for the patient to complete from 2 to 10 breaths; more preferably, the first predetermined period of time is the time required for the patient to complete from 2 to 6 breaths; most preferably, first predetermined period of time is the time required for the patient to complete from 2 to 4 breaths.

In one example, over the third predetermined period of time, if, during the inhalation phase of ventilation, the airway pressure P2 increases acutely and becomes significantly more positive than the trended P1 and P2 pressures, pressure monitoring subsystem 60 will determine that the endotracheal tube 20 is a partially obstructed. In response to this determination, the pressure monitoring subsystem 60 generates a first output signal 70 indicative of a partially obstructed endotracheal tube 20. It is preferred that the pressure monitoring subsystem 60 generates the first output signal 70 if the airway pressure P2 is between approximately 5–25 cm $H_2O$ more positive than the trended P1 and P2 pressures. It is more preferred that the pressure monitoring subsystem 60 generates the first output signal 70 if the airway pressure P2 is between approximately 7–20 cm H$_2$O more positive than the trended P1 and P2 pressures. It is most preferred that the pressure monitoring subsystem 60 generates the first output signal 70 if the airway pressure P2 is between approximately 10–15 cm H$_2$O more positive than the trended P1 and P2 pressures.

In an alternative example, over the third predetermined period of time, if during spontaneous inhalation the tracheal pressure P1 decreases acutely and becomes more negative than the trended P1 and P2 data, then the pressure monitoring subsystem 60 will determine that there is increased endotracheal resistance due to a partial endotracheal tube obstruction and/or a kinked endotracheal tube 20. In response to this determination that patency of the endotracheal tube 20 is degraded, the pressure monitoring subsystem 60 generates a second output signal 72 indicative of increased resistance within the endotracheal tube 20. It is preferred that the pressure monitoring subsystem 60 generates the second output signal 72 if the tracheal pressure P1 is between approximately 1–15 cm H$_2$O more negative than the trended P1 and P2 pressures. It is more preferred that the pressure monitoring subsystem 60 generates the second output signal 72 if the tracheal pressure P1 is between approximately 1–10 cm H$_2$O more negative than the trended P1 and P2 pressures. It is most preferred that the pressure monitoring subsystem 60 generates the second output signal 72 if the tracheal pressure P1 is between approximately 5–10 cm H$_2$O more negative than the trended P1 and P2 pressures.

In yet another example, over the third predetermined period of time, if during spontaneous inhalation the airway pressure P2 decreases acutely and becomes more negative than the trended P2 data, then the pressure monitoring subsystem 60 will determine that there is increased resistance within the ventilator breathing circuit. In response to this determination, the pressure monitoring subsystem 60 generates a third output signal 74 indicative of the increased resistance within the ventilator breathing circuit. It is preferred that the pressure monitoring subsystem 60 generates the third output signal 74 if the airway pressure P2 is between approximately 1–15 cm H$_2$O more negative than the trended P2 pressure. It is more preferred that the pressure monitoring subsystem 60 generates the third output signal 74 if the airway pressure P2 is between approximately 1–10 cm H$_2$O more negative than the trended P2 pressure. It is most preferred that the pressure monitoring subsystem 60 generates the third output signal 74 if the airway pressure P2 is between approximately 1–5 cm H$_2$O more negative than the trended P2 pressure.

Figure 2:
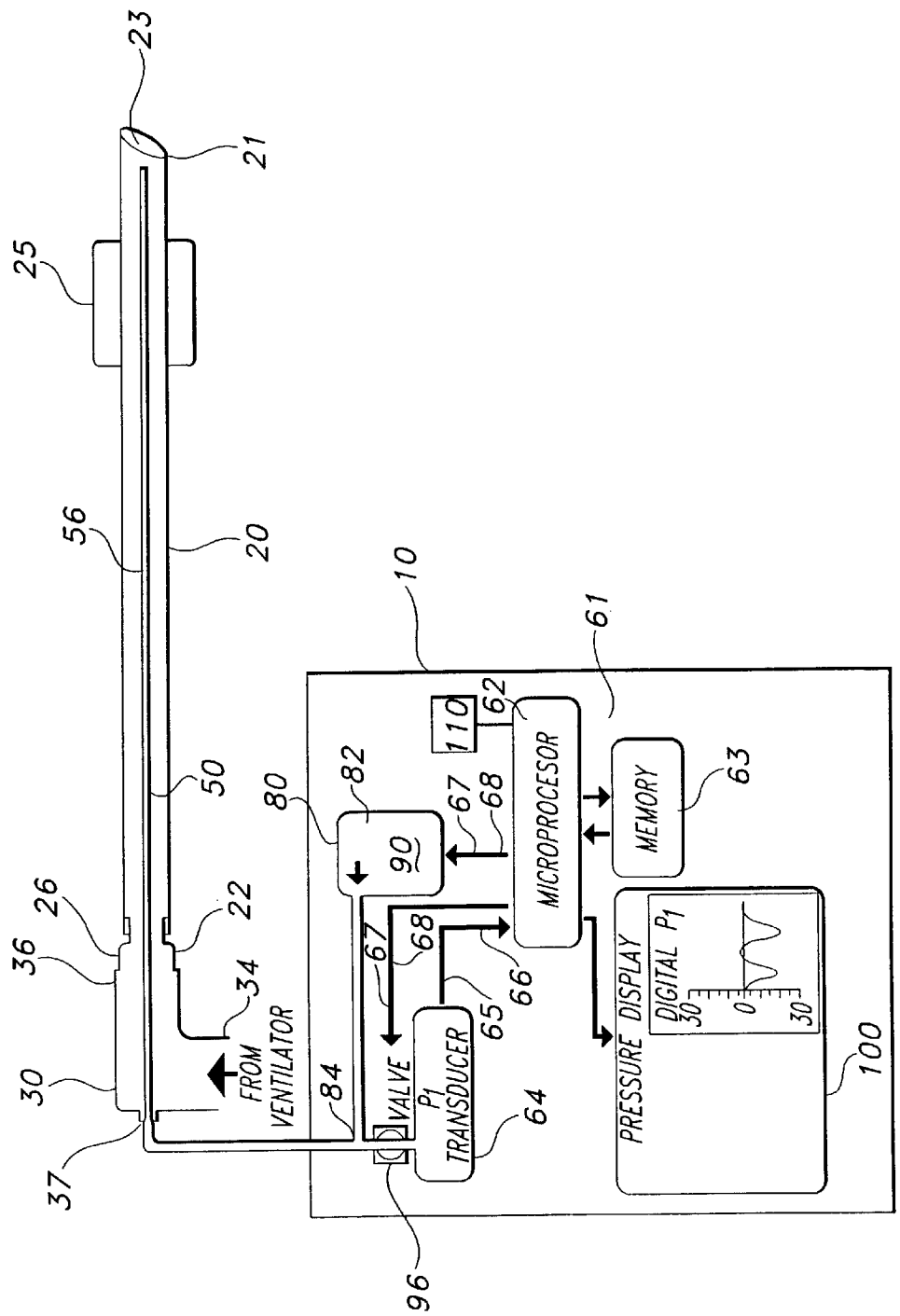
FIG. 2 is a schematic view of a first embodiment of the endotracheal tube pressure monitoring system showing a first pressure line in fluid communication with a distal end of an endotracheal tube and in fluid communication with a purging subsystem.

Referring now to FIG. 2, a first embodiment of an exemplified endotracheal tube pressure monitoring system 10 is shown. Here, the endotracheal tube 20 is connected to the connector 30 which is, in turn, connected to the ventilator. The endotracheal tube 20 is inserted into the trachea of the patient so that the distal end 21 of the endotracheal tube 20 is placed in fluid communication with the trachea of the patient.

The endotracheal tube pressure monitoring system 10 is shown with one pressure line 50. This pressure line 50 is in fluid communication with the distal end 21 of the endotracheal tube 20. Because of the likelihood that the pressure line 50 used in this embodiment will become obstructed due to water or mucus plugs (due to pressure line's 50 proximity to the body fluids in and around the trachea), this example of the system is shown with the pressure line 50 in fluid communication with the purging subsystem 80. The purging subsystem 80 is shown with the source of pressurized fluid 82, for example here a fluid pump 90, in communication with the pressure line 50 at a juncture 84 in the pressure line 50.

The purging actuator 96 is intermediate the juncture 84 and the pressure sensor 64 of the pressure monitoring subsystem 60. Thus, in this example, the tracheal pressure may be monitored and the pressure line 50 may be maintained free from obstructions by activating and deactivating the purging subsystem 80 in response to the response and termination signals 67, 68 generated by the pressure monitoring subsystem 60.

Figure 3:
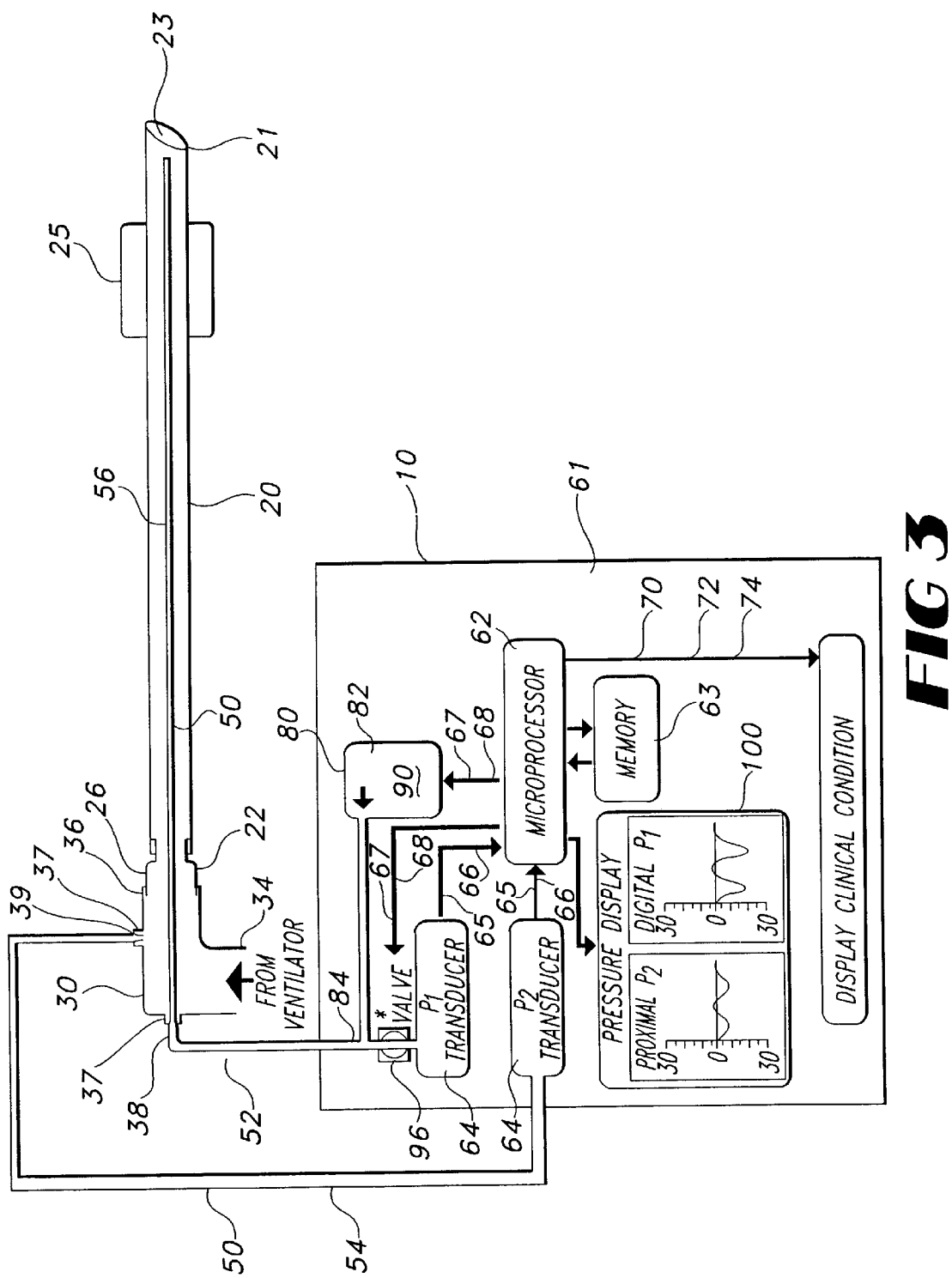
FIG. 3 is a schematic view of a second embodiment of the endotracheal tube pressure monitoring system showing the first pressure line in fluid communication with the distal end of the endotracheal tube and in fluid communication with the purging subsystem, and a second pressure line in fluid communication with a proximal end of the endotracheal tube.

Referring now to FIG. 3, a second embodiment of an exemplified endotracheal tube pressure monitoring system 10 is shown. In this embodiment, the system has a first pressure tube in fluid communication with the distal end 21 of the endotracheal tube 20 and a second pressure tube connected to a port of the connector 30 and in fluid communication with the proximal end 22 of the endotracheal tube 20. Airway pressure may be determined by the fluid within the first pressure line 52 communicating with a first pressure sensor 64 operably attached to the first pressure line 52. Similarly, tracheal pressure may be determined by the fluid within the second pressure line 54 which, is in communication with a second pressure sensor 64 operably attached to the second pressure line 54.

The purging subsystem 80, which includes here, for example, one fluid pump 90, and the first purging actuator 96, is in fluid communication with the first pressure line 52 so that the first pressure line 52 may be maintained free from obstructions by activating and deactivating the purging subsystem 80 in response to a first response signal 67 and a first termination signal 68 generated by the pressure monitoring subsystem 60. The fluid pump 90 is responsive to the first response signal 67 to supply the pressurized fluid to the first pressure line 52 and the first purging actuator 96 is responsive to the first response signal 67 to move to the closed position so that fluid is prevented from being communicated to the first pressure sensor 64. The fluid pump 90 is responsive to the first termination signal 68 to terminated supply of the pressurized fluid to the first pressure line 52 and the first purging actuator 96 is responsive to the first termination signal 68 to move to the open position so that fluid within the first pressure line 52 is in fluid communication with the first pressure sensor 64.

Figure 4:
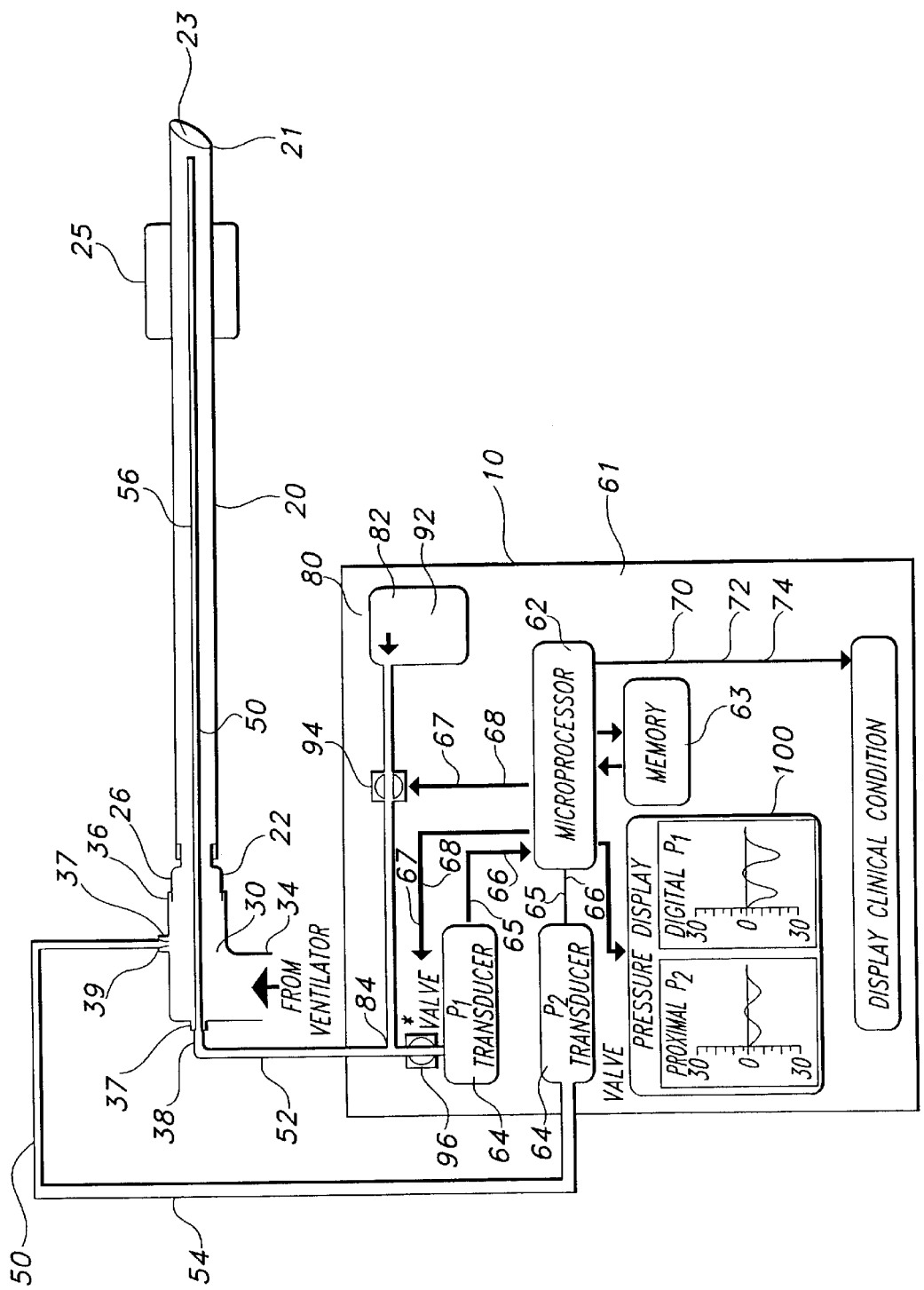
FIG. 4 is a schematic view of a third embodiment of the endotracheal tube pressure monitoring system showing the first pressure line in fluid communication with a vessel of compressed fluid.

Turning now to the third embodiment of an exemplified endotracheal tube pressure monitoring system 10 shown in FIG. 4, the second embodiment described above is shown with the source of pressurized fluid 82 being the vessel of compressed fluid 92 having a fluid actuator 94. Here, the fluid actuator 94 of the vessel 92 is responsive to the first response signal 67 to supply the pressurized fluid to the first pressure line 52 by moving to the open position in which pressurized fluid is communicated from the vessel 92 to the first pressure line 52. Additionally, the first purging actuator 96 is responsive to the first response signal 67 to move to the closed position so that fluid is prevented from being communicated to the first pressure sensor 64. The fluid actuator 94 is responsive to the first termination signal 68 to terminate supply of the pressurized fluid from the vessel 92 to the first pressure line 52 by moving to the closed position in which pressurized fluid from the vessel 92 is not communicated from the vessel 92 to the first pressure line 52. Also, the first purging actuator 96 is responsive to the first termination signal 68 to move to the open position so that fluid within the first pressure line 52 is communicated to the first pressure sensor 64.

Referring to FIG. 5, a fourth embodiment of the endotracheal tube pressure monitoring system 10 is shown. In this embodiment, the system has a first pressure tube in fluid communication with the distal end 21 of the endotracheal tube 20 and a second pressure tube connected to a port of the connector 30 and in fluid communication with the proximal end 22 of the endotracheal tube 20. The airway pressure may be determined by the fluid within the first pressure line 52 communicating with a first pressure sensor 64 operably attached to the first pressure line 52. Similarly, tracheal pressure may be determined by the fluid within the second pressure line 54, which is in communication with a second pressure sensor 64 operably attached to the second pressure line 54.

Here, for example, the purging subsystem 80 includes two fluid pumps 90 and two purging actuators 96. The first fluid pump 90 in fluid communication with the first pressure line 52 and the second fluid pump 90 in fluid communication with the second pressure line 54 and the first and second purging actuators 96 are in fluid communication with the respective first and second pressure lines 52, 54 so that the first and second pressure lines 52, 54 may be maintained free from obstructions. By activating and deactivating the purging subsystem 80 in response to the respective first and second response signals 67 and the respective first and second termination signals 67, 68 generated by the pressure monitoring subsystem 60 when an obstruction is detected in the respective pressure lines. As one skilled in the art will appreciate, the pressure monitoring subsystem 60 will generate the response signal 67 and termination signal 68 for the respective pressure line 52, 54 when the appropriate conditions are met.

The first fluid pump 90 is responsive to the first response signal 67 to supply the pressurized fluid to the first pressure line 52 and the first purging actuator 96 is responsive to the first response signal 67 to move to the closed position so that fluid is prevented from being communicated to the first pressure sensor 64. In like fashion, the second fluid pump 90 is responsive to the second response signal 67 to supply the pressurized fluid to the second pressure line 54 and the second purging actuator 96 is responsive to the second response signal 67 to move to the closed position so that fluid is prevented from being communicated to the second pressure sensor 64. As one skilled in the art will appreciate, the first fluid pump 90 is responsive to the first termination signal 68 to terminated supply of the pressurized fluid to the first pressure line 52 and the first purging actuator 96 is responsive to the first termination signal 68 to move to the open position so that fluid within the first pressure line 52 is in fluid communication with the first pressure sensor 64. In response to the second termination signal 68, the second purging actuator 96 moves to the open position so that fluid within the second pressure line 54 is in fluid communication with the second pressure sensor 64 and the second fluid pump 90 terminates supply of the pressurized fluid to the second pressure line 54.

Referring now to FIG. 6, the fourth embodiment described above and shown in FIG. 5, is illustrated connected to an endotracheal tube 20 having a secondary lumen 56 in the endotracheal tube wall. Here, the second pressure line 54 is shown in operable connection with a port of the connector 30 and in fluid communication with the proximal end 22 of the endotracheal tube 20 for the measurement of the airway pressure. A portion of the first pressure line 52 is formed from the secondary lumen 56 in the endotracheal tube wall, which is in fluid communication with the distal end 21 of the endotracheal tube 20 and the remaining portion of the first pressure line 52 is formed by the connection of the connector tube 58.

The fifth embodiment of the exemplified endotracheal tube pressure monitoring system 10 shown in FIG. 7, is different from the fourth embodiment described above and illustrated in FIG. 5 because the source of pressurized fluid 82 shown is the vessel of compressed fluid 92 having a plurality of fluid actuators 92. Here, for example, the fluid actuators 92 include a first fluid actuator 94 and a second fluid actuator 94. The first fluid actuator 94 of the vessel 92 is responsive to the first response signal 67 to supply the pressurized fluid to the first pressure line 52 by moving to the open position in which pressurized fluid is communicated from the vessel 92 to the first pressure line 52. In a similar fashion, the second fluid actuator 94 of the vessel 92 is responsive to the second response signal 67 to supply the pressurized fluid to the second pressure line 54 by moving to the open position in which pressurized fluid is communicated from the vessel 92 to the second pressure line 54.

Still referring to FIG. 7, to protect the potentially fragile first and second pressure sensors 64, the first and second purging actuators 96 are responsive to the respective first and second response signals 67 to move to the closed position so that pressurized fluid being supplied to the respective first and second pressure lines 52, 54 is prevented from being communicated to the respective first and second pressure sensors 64.

The first fluid actuator 94 is responsive to the first termination signal 68 to terminate supply of the pressurized fluid from the vessel 92 to the first pressure line 52 by moving to the closed position, in which pressurized fluid from the vessel 92 is not communicated from the vessel 92 to the first pressure line 52. At substantially the same time, the first purging actuator 96 is responsive to the first termination signal 68 to move to the open position so that fluid within the first pressure line 52 is communicated to the first pressure sensor 64. For the second pressure line 54, the second fluid actuator 94 is responsive to the second termination signal 68 to terminate supply of the pressurized fluid from the vessel 92 to the second pressure line 54. The second fluid actuator 94 is moved to the closed position in which pressurized fluid from the vessel 92 may not be communicated from the vessel 92 to the second pressure line 54. At substantially the same time, the second purging actuator 96 is responsive to the second termination signal 68 to move to the open position so that fluid within the second pressure line 54 is communicated to the second pressure sensor 64.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endotracheal tube pressure monitoring system comprising:
 a. an endotracheal tube having an open distal end, an opposing open proximal end, and a major lumen extending within the tube from the proximal end to the distal end, the distal end of the tube in fluid communication with a trachea of a patient;
 b. at least one pressure line in fluid communication with the major lumen of the endotracheal tube;
 c. a purging subsystem in fluid communication with at least one pressure line; and d. a pressure monitoring subsystem in operative communication with each respective pressure line, the pressure monitoring subsystem having means to monitor the pressure of fluid within each respective pressure line, wherein, for each pressure line in fluid communication with the purging subsystem, the pressure monitoring subsystem generates a response signal after a first predetermined time period in which pressure within the pressure line with which the purging subsystem is in fluid communication remains substantially constant, and wherein the purging subsystem is responsive to the response signal of the pressure monitoring subsystem to supply a pressurized fluid to the pressure line with which the purging subsystem is in fluid communication for a second predetermined time period after generation of the response signal.

2. The endotracheal tube pressure monitoring system of claim 1, wherein the pressure monitoring subsystem generates a termination signal after the second predetermined time period, and wherein the purging subsystem is responsive to the termination signal of the pressure monitoring subsystem to terminate supply of the pressurized fluid to the pressure line with which the purging subsystem is in fluid communication.

3. The endotracheal tube pressure monitoring system of claim 2, wherein the purging subsystem comprises:
   a. at least one source of pressurized fluid; and
   b. at least one purging actuator, the source of pressurized fluid being in fluid communication with at least one pressure line at a juncture in the respective pressure line, wherein one purging actuator is operatively connected to the pressure line intermediate the pressure sensor and the juncture, and wherein the purging actuator, responsive to the response signal and the termination signal, is movable between an open position, in which fluid within the pressure line is communicated to the pressure sensor, and a closed position, in which fluid is prevented from being communicated to the pressure sensor.

4. The endotracheal tube pressure monitoring system of claim 3, wherein the source of pressurized fluid is a fluid pump that is responsive to the response signal to supply the pressurized fluid and is also responsive to the termination signal to terminate supply of the pressurized fluid.

5. The endotracheal tube pressure monitoring system of claim 3, wherein the source of pressurized fluid is a vessel of compressed fluid having a fluid actuator, and wherein the fluid actuator, responsive to the response signal and the termination signal, is movable between a closed position, in which the pressurized fluid is shut off from the pressure line, and an open position, in which the pressurized fluid is communicated to the pressure line.

6. The endotracheal tube pressure monitoring system of claim 1, wherein the at least one pressure line includes a first pressure line in fluid communication with the distal end of the endotracheal tube, and wherein the purging subsystem is in fluid communication with the first pressure line.

7. The endotracheal tube pressure monitoring system of claim 6, wherein the at least one pressure line includes a second pressure line in fluid communication with the proximal end of the endotracheal tube.

8. The endotracheal tube pressure monitoring system of claim 7, wherein the purging subsystem is in fluid communication with the second pressure line.

9. The endotracheal tube pressure monitoring system of claim 1, wherein the pressure monitoring means of the pressure monitoring subsystem comprises:
   a. at least one pressure sensor; and
   b. a computing apparatus connected to each respective pressure sensor, wherein each pressure line has one pressure sensor operatively attached for sensing the pressure of the fluid within each respective pressure line.

10. An endotracheal tube pressure monitoring system comprising:
   a. an endotracheal tube having an open proximal end, an opposing open distal end, and a major lumen extending within the tube from the proximal end to the distal end, the distal end of the endotracheal tube in fluid communication with a trachea of a patient;
   b. a first pressure line in fluid communication with the distal end of the endotracheal tube;
   c. a second pressure line in fluid communication with the proximal end of the endotracheal tube;
   d. a pressure monitoring subsystem in operative communication with the first pressure line and the second pressure line, the pressure monitoring subsystem having a first pressure sensor for sensing the pressure of the fluid within the first pressure line, a second pressure sensor for sensing the pressure within the second pressure line, and a computing apparatus connected to the first pressure sensor and the second pressure sensor; and
   e. a purging subsystem in fluid communication with the first pressure line, wherein the computing apparatus of the pressure monitoring subsystem generates a first response signal after a first predetermined time period in which pressure within the first pressure line remains substantially constant and generates a first termination signal after a second predetermined time period after the generation of the first response signal, wherein the purging subsystem is responsive to the first response signal to supply a pressurized fluid to the first pressure line, and wherein the purging subsystem is responsive to the first termination signal to terminate supply of the pressurized fluid to the first pressure line.

11. The endotracheal tube pressure monitoring system of claim 10, wherein the purging subsystem comprises:
   a. a source of pressurized fluid in fluid communication with the first pressure line at a first juncture in the first pressure line; and
   b. a first purging actuator intermediate the first pressure sensor and the first juncture, wherein the first purging actuator, responsive to the first response signal and the first termination signal, is movable between an open position, in which fluid within the first pressure line is communicated to the first pressure sensor, and a closed position, in which fluid is prevented from being communicated to the first pressure sensor.

12. The endotracheal tube pressure monitoring system of claim 11, wherein the source of pressurized fluid is a fluid pump, wherein the fluid pump is responsive to the first response signal to supply the pressurized fluid to the first pressure line, and wherein the fluid pump is responsive to the first termination signal to terminate supply of the pressurized fluid to the first pressure line.

13. The endotracheal tube pressure monitoring system of claim 11, wherein the source of pressurized fluid is a vessel of compressed fluid having a fluid actuator, and wherein the fluid actuator, responsive to the response signal, is movable between a closed position, in which the pressurized fluid is shut off from the vessel to the pressure line, and an open position, in which pressurized fluid is communicated from the vessel to the pressure line.

14. The endotracheal tube pressure monitoring system of claim 11, wherein the source of pressurized fluid is in fluid communication with the second pressure line, wherein the computing apparatus of the pressure monitoring subsystem generates a second response signal after the first predetermined time period in which pressure within the second pressure line remains substantially constant and generates a second termination signal after the second predetermined time period after the generation of the second response signal, wherein the purging subsystem is responsive to the second response signal to supply the pressurized fluid to the second pressure line, and wherein the purging subsystem is responsive to the second termination signal to terminate supply of the pressurized fluid to the second pressure line.

15. The endotracheal tube pressure monitoring system of claim 14, wherein the purging subsystem has a second purging actuator, wherein the source of pressurized fluid is responsive to the second response signal and is in fluid communication with the second pressure line at a second juncture in the second pressure line, the second purging actuator intermediate the second pressure sensor and the second juncture, wherein the second purging actuator, responsive to the second response signal and the second termination signal, is movable between an open position, in which fluid within the second pressure line is communicated to the second pressure sensor, and a closed position, in which fluid is prevented from being communicated to the second pressure sensor.

16. The endotracheal tube pressure monitoring system of claim 15, wherein the source of pressurized fluid includes a first fluid pump and a second fluid pump, wherein the first fluid pump is in fluid communication with the first pressure line to supply the pressurized fluid to the first pressure line in response to the first response signal, wherein the first fluid pump is responsive to the first termination signal to terminate supply of the pressurized fluid to the first pressure line, wherein the second fluid pump is in fluid communication with the second pressure line to supply the pressurized fluid to the second pressure line in response to the second response signal, and wherein the second fluid pump is responsive to the second termination signal to terminate supply of the pressurized fluid to the second pressure line.

17. The endotracheal tube pressure monitoring system of claim 15, wherein the source of pressurized fluid is a vessel of compressed fluid having a plurality of fluid actuators, wherein the plurality of fluid actuators include a first fluid actuator and a second fluid actuator, wherein the first fluid actuator is intermediate the first juncture and the vessel of compressed liquid and is responsive to the first response signal and the first termination signal, the first fluid actuator movable between a closed position, in which the pressurized fluid is not communicated to the first pressure line, and an open position, in which the pressurized fluid is communicated to the first pressure line, and wherein the second fluid actuator is intermediate the second juncture and the vessel of compressed liquid and is responsive to the second response signal and the second termination signal, the second fluid actuator movable between a closed position, in which the pressurized fluid is not communicated to the second pressure line, and an open position, in which the pressurized fluid is communicated to the second pressure line.

18. The endotracheal tube pressure monitoring system of claim 10, wherein at least a portion of the first pressure line is formed from a secondary lumen, the secondary lumen extending within the endotracheal tube from the distal end of the endotracheal tube.

19. The endotracheal tube pressure monitoring system of claim 18, wherein the secondary lumen is a catheter.

20. The endotracheal tube pressure monitoring system of claim 18, further comprising a connector having a first end, an opposing second end, a tubular conduit extending between the first and second end, and a first port in communication with the tubular conduit, wherein the connector has an inside diameter sized to provide a frictional fit between the first end and a Y-connector of a ventilator breathing circuit and to provide a frictional fit between the second end and the proximal end of the endotracheal tube, and wherein the secondary lumen extends through the first port to the distal end of the endotracheal tube.

21. The endotracheal tube pressure monitoring system of claim 20, wherein the connector has a second port in communication with the tubular conduit, and wherein a proximal end of the second pressure line is connected to the second port.

22. The endotracheal tube pressure monitoring system of claim 10, further comprising a connector having a first end, an opposing end, a tubular conduit extending between the first and second end, and a first port in communication with the tubular conduit, wherein the connector has an inside diameter sized to provide a frictional fit between the first end and a Y-connector of a ventilator breathing circuit and to provide a frictional fit between the second end and the proximal end of the endotracheal tube, and wherein a proximal end of the second pressure line is connected to the first port.

23. A method of monitoring the pressure of fluid at a distal and proximal end of an endotracheal tube, the method comprising:

a. providing an endotracheal tube having an open proximal end, an opposing open distal end, and a major lumen extending within the tube from the proximal end to the distal end;

b. inserting the endotracheal tube into a trachea of a patient, the distal end of the endotracheal tube is in fluid communication with the trachea of the patient;

c. measuring the pressure of the fluid within a first pressure line which is in fluid communication with the distal end of the endotracheal tube;

d. measuring the pressure of the fluid within a second pressure line which is in fluid communication with the proximal end of the endotracheal tube;

e. determining an obstruction status of the first pressure line by monitoring the measured pressure of the fluid within the first pressure line and generating a first response signal if the measured pressure of the fluid in the first pressure line remains generally constant for a first predetermined period of time;

f. activating a purging subsystem, in response to the first response signal, to supply a pressurized fluid to the first pressure line;

g. generating a first termination signal a second predetermined period of time after the first response signal is generated; and h. deactivating the purging subsystem, in response to the first termination signal, to terminated supply of the pressurized fluid to the first pressure line.

24. The method of claim 23, wherein the pressure of the fluid within the first pressure line is measured by a first pressure sensor in communication with a distal end of the first pressure line, wherein the purging subsystem comprises a source of pressurized fluid in communication with the first pressure line at a first juncture in the first pressure line and a first purging actuator intermediate the first pressure sensor and the first juncture, wherein the first purging actuator is movable between an open position, in which fluid within the first pressure line is communicated to the first pressure sensor, and a closed position, in which fluid is prevented from being communicated to the first pressure sensor, and wherein, in response to the first response signal, the first purging actuator is positioned in the closed position for the second predetermined period of time and, upon the elapse of the second predetermined period of time, in response to the first termination signal, the first purging actuator returns to the open position.

25. The method of claim 24, further comprising:
   a. determining the obstruction status of the second pressure line by monitoring the measured pressure of the fluid within the second pressure line and generating a second response signal if the measured pressure of the fluid in the second pressure line remains constant for the first predetermined period of time;
   b. activating the purging subsystem, in response to the second response signal, to supply pressurized fluid to the second pressure line;
   c. generating a second termination signal the second predetermined time after the second response signal is generated; and
   d. deactivating the purging subsystem, in response to the second termination signal, to terminated supply of the pressurized fluid to the second pressure line.

26. The method of claim 25, wherein the pressure of the fluid within the second pressure line is measured by a second pressure sensor in communication with the second pressure line, wherein the purging subsystem is in fluid communication with the second pressure line at a second juncture intermediate in second pressure line, and wherein the purging subsystem has a second purging actuator, the second purging actuator intermediate the second pressure sensor and the second juncture, wherein the second purging actuator is movable between an open position, in which fluid within the second pressure line is communicated to the second pressure sensor, and a closed position, in which fluid is prevented from being communicated to the second pressure sensor, wherein, in response to the second response signal, the second purging actuator is positioned in the closed position for the second predetermined period of time and, upon the elapse of the second predetermined period of time, in response to the second termination signal, the second purging actuator returns to the open position.

27. The method of claim 23, further comprising displaying the pressure of the fluid measured within the first pressure line and the second pressure line.

28. The method of claim 23, further comprising:
   a. determining a partial obstruction status of the endotracheal tube by monitoring the measured pressure of the fluid within the first and second pressure lines and determining a trend pressure within the first and second pressure lines over a third predetermined period of time from the measured pressure of the fluid within the first and second pressure lines, and
   b. displaying a partial endotracheal obstruction status message if the measured pressure of the fluid in the second pressure line increases above the trend pressure of the fluid within the first and second pressure lines.

29. The method of claim 23, further comprising:
   a. determining an increase in resistance of the endotracheal tube by monitoring the measured pressure of the fluid within the first and second pressure lines and determining a trend pressure within the first and second pressure lines over a third predetermined period of time from the measured pressure of the fluid within the first and second pressure lines; and
   b. displaying an endotracheal tube patency alert message if the measured pressure within the first pressure line decreases below the trend pressure of the fluid within the first and second pressure lines.

30. The method of claim 23, further comprising:
   a. determining an increase in resistance of a ventilator breathing circuit by monitoring the measured pressure of the fluid within the second pressure line and determining a trend pressure within the second pressure line over a third predetermined period of time from the measured pressure of the fluid within the second pressure line; and
   b. displaying a ventilator breathing circuit resistance alert if the measured pressure within the second pressure line becomes lower than the trend pressure of the fluid within the second pressure line.

* * * * *